US010288584B2

(12) United States Patent
Shigetomi et al.

(10) Patent No.: US 10,288,584 B2
(45) Date of Patent: May 14, 2019

(54) METHOD FOR LOCATING MACHINING POSITION IN REPAIR MATERIAL, AND REPAIRING METHOD

(71) Applicant: MITSUBISHI AIRCRAFT CORPORATION, Aichi (JP)

(72) Inventors: Toshikazu Shigetomi, Tokyo (JP); Masatsugu Shimizu, Tokyo (JP); Ryuichi Nagase, Tokyo (JP); Morimasa Ishida, Aichi (JP); Shuhei Muto, Aichi (JP)

(73) Assignee: MITSUBISHI AIRCRAFT CORPORATION, Aichi (JP)

( * ) Notice: Subject to any disclaimer, the term of this patent is extended or adjusted under 35 U.S.C. 154(b) by 309 days.

(21) Appl. No.: 14/875,982

(22) Filed: Oct. 6, 2015

(65) Prior Publication Data

US 2016/0137316 A1  May 19, 2016

(30) Foreign Application Priority Data

Nov. 13, 2014 (JP) .................................. 2014-230689

(51) Int. Cl.
*B23P 6/00* (2006.01)
*B64F 5/40* (2017.01)
(Continued)

(52) U.S. Cl.
CPC ................ *G01N 29/07* (2013.01); *B23P 6/00* (2013.01); *B29C 70/00* (2013.01); *B29C 73/105* (2013.01);
(Continued)

(58) Field of Classification Search
CPC ......... Y10T 29/49732; Y10T 29/49734; Y10T 29/49746; Y10T 29/49769;
(Continued)

(56) References Cited

U.S. PATENT DOCUMENTS 4,309,904 A * 1/1982 Jones ...................... G06K 19/06
73/597
4,457,174 A * 7/1984 Bar-Cohen ........... G01N 29/223
73/582
(Continued)

FOREIGN PATENT DOCUMENTS

FR      2520455 A1 *  7/1983 ............ F16B 37/122
JP      2013-28332 A    2/2013
JP      2014-100847 A   6/2014

OTHER PUBLICATIONS

Translation of FR2520455A1, generated Aug. 16, 2018.*

*Primary Examiner* — Matthew P Travers
(74) *Attorney, Agent, or Firm* — Pearne & Gordon LLP (57) ABSTRACT

The present invention provides a method for locating a machining position in a repair material that is arranged on a member including a machined portion formed by predetermined machining, the method including: a step of arranging a marker including a portion having a different propagation characteristic of an ultrasonic wave from that of a peripheral portion in the machined portion existing in the member before the repair material is arranged on the member; and a step of applying the ultrasonic wave to the member covered with the repair material and locating the machining position at a position of the marker captured by the ultrasonic wave after the repair material is arranged on the member.

17 Claims, 7 Drawing Sheets

(51) Int. Cl.
    *B64F 5/60*     (2017.01)
    *B29C 70/00*     (2006.01)
    *B29C 73/10*     (2006.01)
    *B29C 73/26*     (2006.01)
    *G01N 29/04*     (2006.01)
    *G01N 29/07*     (2006.01)
    *G01N 29/24*     (2006.01)
    *G01N 29/44*     (2006.01)

(52) U.S. Cl.
    CPC ............... *B64F 5/40* (2017.01); *B64F 5/60* (2017.01); *G01N 29/043* (2013.01); *G01N 29/048* (2013.01); *G01N 29/2475* (2013.01); *G01N 29/4436* (2013.01); *B23B 2215/04* (2013.01); *B23B 2270/10* (2013.01); *B23B 2270/48* (2013.01); *B23P 2700/01* (2013.01); *B29C 73/10* (2013.01); *B29C 2073/264* (2013.01); *G01N 2291/2694* (2013.01)

(58) Field of Classification Search
    CPC ......... Y10T 29/49774; Y10T 29/49778; Y10T 29/49993; B23P 6/00; B23P 6/04; B23P 2700/06; B23P 2700/01; B23B 49/00; B23B 2215/04; B23B 2270/10; B23B 2270/34; B23B 2270/48; B23B 2270/54; B64F 5/40; B64F 5/60; G01N 29/00; G01N 29/048; G01N 2291/0231; G01N 2291/2694; G01N 29/043; G01N 29/07; G01N 2291/0289; G01N 29/2475; G01S 15/06; G01S 15/88
    See application file for complete search history.

(56) References Cited

U.S. PATENT DOCUMENTS

| | | | |
|---|---|---|---|
| 5,190,611 A * | 3/1993 | Cologna | B29C 73/063 156/94 |
| 5,413,269 A * | 5/1995 | Aja | G01N 29/30 228/104 |
| 9,669,113 B1 * | 6/2017 | Sirimanne | A61K 49/006 |
| 2009/0088635 A1 * | 4/2009 | Fisher | A61B 90/39 600/437 |
| 2013/0014367 A1 | 1/2013 | Miller et al. | |
| 2013/0307174 A1 * | 11/2013 | Lindgren | B23Q 17/20 264/40.1 |
| 2014/0141190 A1 | 5/2014 | Shigetomi et al. | |

* cited by examiner

METHOD FOR LOCATING MACHINING POSITION IN REPAIR MATERIAL, AND REPAIRING METHOD

BACKGROUND OF THE INVENTION

Field of the Invention

The present invention relates to a method for locating a machining position, which enables to apply machining originally applied to a repair target to a repair material used for repair at the same position.

Description of the Related Art

When an airframe of aircraft formed from a composite material is repaired, a composite patch is arranged in a recessed portion formed by scraping away a damaged point, and is shaped by curing the composite patch and an adhesive by heating while drawing a vacuum (for example, Japanese Patent Laid-Open No. 2014-100847). Ultrasonic testing is performed in order to examine a state of damage before repair, a quality after repair, or the like in a nondestructive manner.

A method for generating a design of a repair member for efficiently repairing an extensive repair region has been proposed (Japanese Patent Laid-Open No. 2013-28332).

When a fastener that fastens airframe parts is included in the repair region, a through-hole into which the fastener is inserted is machined in the composite patch after the composite patch is shaped by curing. At this time, it is necessary to form a hole at the same position as an original through-hole left on a back side of the composite patch. However, since the original through-hole is concealed by the composite patch, the original through-hole cannot be seen.

Thus, a distance from a distinctive portion of the airframe to the fastener in the repair region is measured in advance, and a hole machining position on the composite patch is located based on the distance. Alternatively, the hole machining position is located by fabricating a positioning jig.

In the case in which the distance from a distinctive portion of the airframe to the fastener in the repair region is measured, an appropriate distinctive portion does not always exist near the fastener, and an error proportional to the distance is included in a measurement value. There is also a possibility that an artificial measurement error occurs.

On the other hand, when the positioning jig is used, location accuracy is high. However, it is necessary to fabricate a jig corresponding to a repair target every time, so that it takes time and cost for the repair.

Thus, an object of the present invention is to provide a method that enables to accurately locate a machining position in a repair material while reducing a time and a cost required for repair.

SUMMARY OF THE INVENTION

The present invention is a method for locating a machining position in a repair material that is arranged on a member including a machined portion formed by predetermined machining, the method including: a step of arranging a marker including a portion having a different propagation characteristic of an ultrasonic wave from that of a peripheral portion in the machined portion existing in the member, or ensuring a hollow in the machined portion before the repair material is arranged on the member; and a step of applying the ultrasonic wave to the member covered with the repair material and locating the machining position at a position of the marker captured by the ultrasonic wave after the repair material is arranged on the member.

In accordance with the present invention, it is possible to easily locate the machining position by ultrasonic testing by using the marker or the hollow ensured in the machined portion without fabricating an expensive jig or without measuring a distance from a distinctive portion of an airframe to the machined portion.

The repair material in the present invention can include a repair patch that covers the member, and an adhesive that bonds the repair patch to the member that is a repair target.

In the present invention, the marker including air may be used.

Since the air has a very different wave propagation characteristic from those of materials of the repair material and the repair target member, it is possible to easily locate the accurate machining position at the position of the marker that is made visible by the ultrasonic testing.

In a case in which the machined portion is a through-hole that passes through the member or a hole that is formed in the member, an inside of the machined portion may be entirely filled and sealed by the marker and a seal material before the repair material is arranged on the member. Accordingly, when a damaged point is cut off, a tool is not caught on an edge of the machined portion, and the damaged point can be cut off in a desired shape.

In a case in which the machined portion is a through-hole that passes through the member or a hole that is formed in the member similarly to the above case, the marker may have an indicating member in a form pointing to an axial center of the marker, or a hollow in a form pointing to the axial center.

The indicating member or the hollow in the above form indicates an axial center of the through-hole or the hole based on a difference in a wave propagation characteristic with its peripheral portion. Thus, it is possible to accurately locate the machining position.

The present invention is particularly suitable for a case in which the repair material having a repair patch formed from a fiber reinforced resin before curing is used. If a machined portion is formed in the repair patch (called a prepreg) in advance, a shape of the machined portion is changed when the repair patch is joined to the member by heat-curing. It is thus necessary to machine the repair patch after the repair patch is joined. In accordance with the present invention, it is possible to locate a position of the machined portion covered with the repair patch by the ultrasonic testing by using the marker after the repair patch is joined.

A repairing method of the present invention including the above method for locating a machining position is a method using a repair material that is arranged on a member including a machined portion formed by predetermined machining, the method including: a first step of arranging a marker including a portion having a different propagation characteristic of an ultrasonic wave from that of a peripheral portion in the machined portion existing in the member before the repair material is arranged on the member; a second step of joining the repair material to the member; a third step of applying the ultrasonic wave to the member covered with the repair material and locating the machining position at a position of the marker captured by the ultrasonic wave; and a fourth step of applying machining to the machining position of at least the repair material out of the repair material and the member.

In accordance with the present invention, a repair target can be restored by correctly applying machining to the same machining position as an original position.

In a case in which the machined portion existing in the member is a through-hole that passes through the member, it is preferable that the method includes a sealing step of sealing an inside of the through-hole by a seal material before the repair material is arranged on the member, in the second step, the repair material is cured by heating while a pressure between the repair material and the member is being reduced, and in the fourth step, the marker and the seal material are removed by applying machining to the machining position throughout the repair material and the member.

The pressure reduction in the heating is enabled by sealing the through-hole. It is possible to surely join the repair material to the member by pressing the repair material against the member by a pressure difference with an atmospheric pressure.

It is also possible to remove the seal material and the marker at the same time as applying machining to the located machining position.

In the above sealing step, the inside of the through-hole is preferably filled entirely and sealed by the marker and the seal material.

Accordingly, when a damaged point is cut off, a tool is not caught on an edge of the through-hole, and the damaged point can be cut off in a desired shape.

In another method for locating a machining position of the present invention, the machined portion is a through-hole that passes through the member, or a hole that is formed in the member, a hollow is left within the machined portion after the repair material is arranged on the member, and the method includes a step of applying an ultrasonic wave to the member covered with the repair material, and locating the machining position at a position of the hollow captured by the ultrasonic wave.

The hollow left in a portion or the whole of the machined portion functions similarly to the above marker.

In other words, when the hollow is not left within the machined portion, the position of the machined portion can be indicated by the above marker.

The method for locating a machining position in a repair material, and the repairing method described above are suitable for repairing a member that constitutes an aircraft.

In accordance with the present invention, it is possible to accurately locate the machining position in the repair material while reducing a time and a cost required for the repair.

BRIEF DESCRIPTION OF THE DRAWINGS

FIGS. 5A-5C show preferable markers in which FIG. 5A and FIG. 5C are plan views and FIG. 5B is a perspective view;

DETAILED DESCRIPTION OF THE PREFERRED EMBODIMENTS

In the following, an embodiment of the present invention will be described by reference to the accompanying drawings.

In the present embodiment, repair of a composite material that is used for an airframe of an aircraft is described.

In the present specification, the "composite material" means a fiber reinforced resin containing reinforcing fibers such as carbon fibers and glass fibers.

In the present embodiment, repair in a case in which a through-hole into which a fastener is inserted is included in a region of the airframe subjected to the repair is described.

Figure 1A:
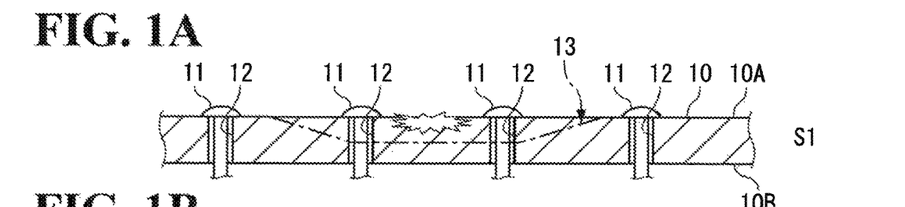
FIGS. 1A-1F are views for explaining repair steps according to an embodiment of the present invention.

FIG. 1A shows a panel 10 that is formed from a composite material. The panel 10 includes a plurality of layers laminated by an appropriate number according to a required thickness. Each of the layers is composed of a sheet-shaped fiber substrate, and a resin impregnated into the fiber substrate.

The panel 10 may be also formed from a metal material such as aluminum alloy.

The panel 10 is fastened to another member (not shown) by fasteners 11. A through-hole 12 into which each of the fasteners 11 is inserted is formed in the panel 10 along a thickness direction.

When the panel 10 is damaged by an impact, it is necessary to perform repair in a region necessary for ensuring sufficient strength/stiffness, including a damaged point.

In the repair, ultrasonic testing is performed to examine a state of damage within the panel 10. For example, delamination is considered as the damage within the panel 10 made of the composite material.

Figure 1D:
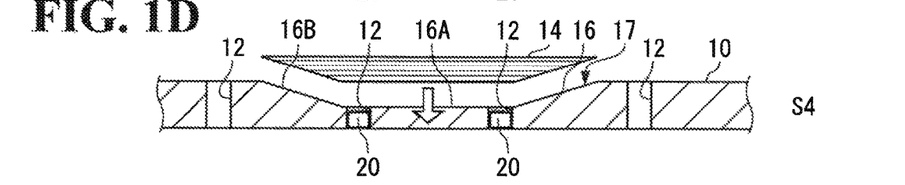
Figure 2:
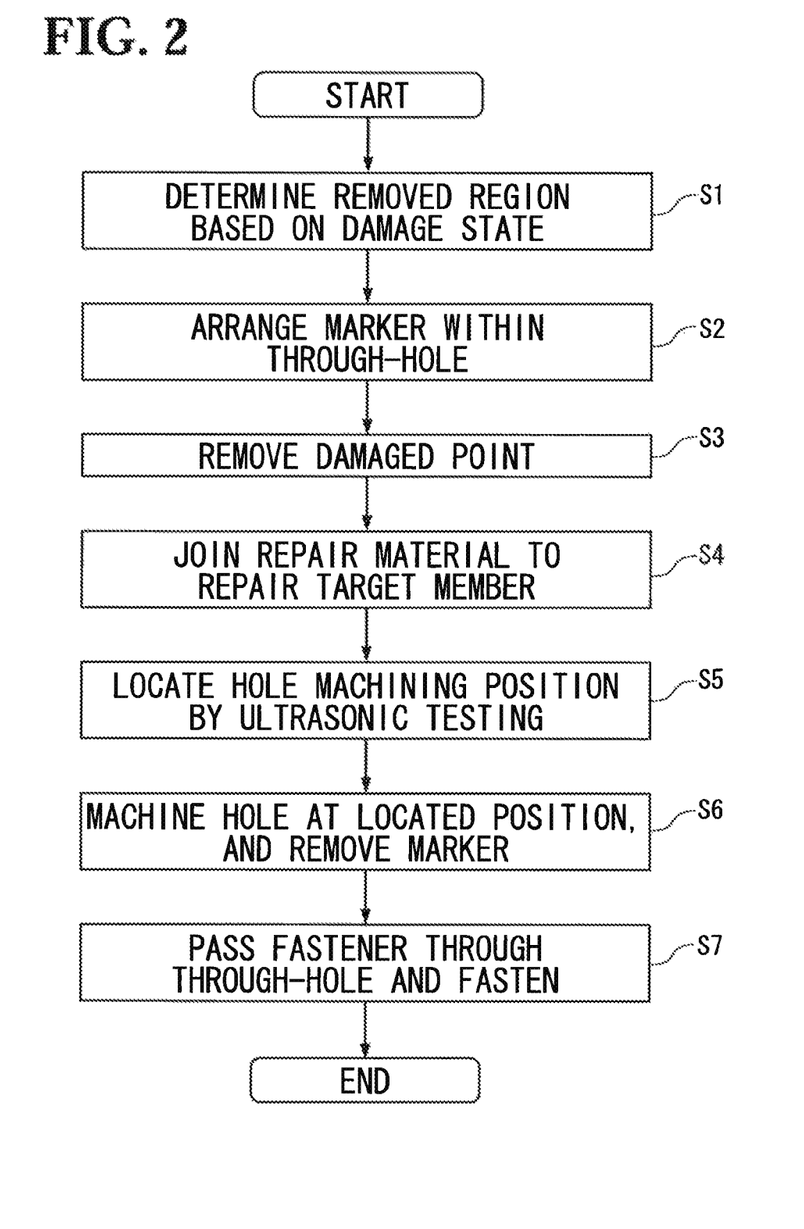
FIG. 2 is a flowchart illustrating the repair steps according to the embodiment of the present invention.

A region 13 (an upper side of an alternate long and short dash line in FIG. 1A) in which the panel 10 is scraped away and removed is determined based on a size, a position, and a degree of the damage obtained by the ultrasonic testing (FIG. 2, step S1). The removed region 13 includes the entire damage. A removed portion is replaced with a repair patch 14 (FIG. 1D) formed from a composite material.

Figure 1B:
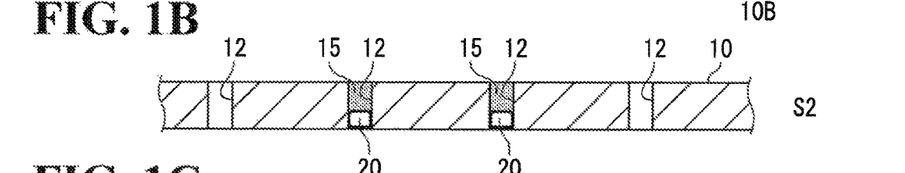

Before the damaged point is scraped away, the inside of the through-hole 12 that is at least partially included in the removed region 13 (FIG. 1A) is entirely filled with a resin material 15 as shown in FIG. 1B. At this time, a marker 20 is arranged within the through-hole 12, and is embedded in the resin material 15 (FIG. 2: step S2).

The resin material 15 is formed by putting a resin material having fluidity into the through-hole 12, and curing the resin material. The cured resin material 15 has heat resistance enough to retain its shape even when the repair patch 14 is heated.

Since the inside of the through-hole 12 is sealed by the resin material 15, vacuum drawing can be performed when the repair patch 14 is heated.

Figure 3A:
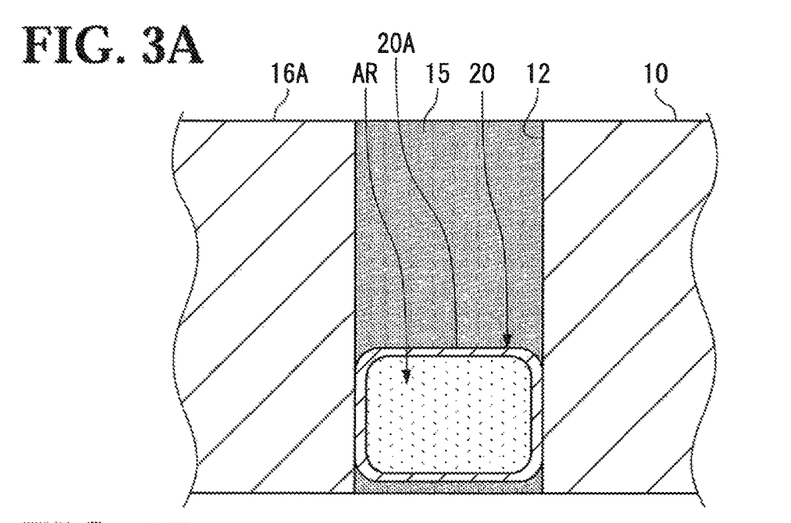
FIG. 3A is a view illustrating a state in which a through-hole included in a repair region of a member is filled with a marker and a resin material.
Figure 3B:
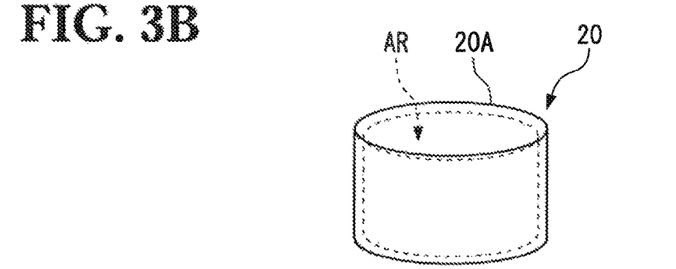
FIG. 3B is a perspective view illustrating the marker.

The marker 20 indicates a position where a hole continuing to the through-hole 12 is machined in the repair patch 14. As shown in FIGS. 3A and 3B, the marker 20 includes air AR within a substantially-cylindrical outer shell 20A. An upper end and a lower end of the outer shell 20A are closed, and a hollow is formed within the outer shell 20A. The outer shell 20A can be formed from any material such as resin and metal.

The marker 20 is arranged within the through-hole 12 before the repair patch 14 (FIG. 1D) is arranged and joined to the panel 10 in order to subsequently locate a position of the through-hole 12 through which the fastener 11 is passed. The marker 20 is installed within the through-hole 12 so as to be positioned below the removed region 13 of the panel 10 in the through-hole 12. It is preferable to substantially align an axial center of the outer shell 20A with a hole axis (an axial center) of the through-hole 12.

The marker 20 has heat resistance enough to retain its shape even when the repair patch 14 is heated, and keep a state in which the air AR is included. After the repair patch 14 is joined to the panel 10, a position where a hole is to be machined in the repair patch 14 is located by ultrasonic testing by using the marker 20.

Figure 1C:
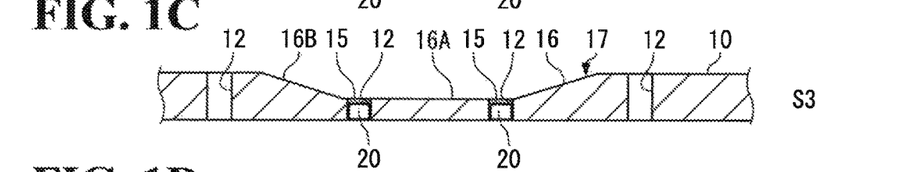

In a state in which the through-hole 12 is filled with the resin material 15, the damaged point is scraped away and removed by using a tool (FIG. 1C, FIG. 2: step S3). Accordingly, the tool is not caught on an edge of the through-hole 12, and a desired cut surface 16 having a truncated cone shape can be obtained. In order to ensure a sufficient junction area between the repair patch 14 and the base material (the panel 10), the cut surface 16 is formed at a gentle inclination angle.

Although the through-hole 12 is positioned in a bottom surface 16A of the cut surface 16 in FIG. 1, the through-hole 12 may be positioned in a slanting surface 16B of the cut surface 16.

Subsequently, the repair patch 14 corresponding to the shape of the cut surface 16 is prepared, is arranged within a recessed portion 17 surrounded by the cut surface 16, and is joined to the panel 10 (FIG. 1D, FIG. 2: step S4).

The repair patch 14 is formed from a prepreg before curing. The prepreg includes a plurality of layers laminated by an appropriate number according to a depth of the recessed portion 17. Each of the layers is composed of a sheet-shaped fiber substrate, and a thermosetting resin such as epoxy, polyimide, polyurethane, and unsaturated polyester resins impregnated into the fiber substrate.

Figure 4A:
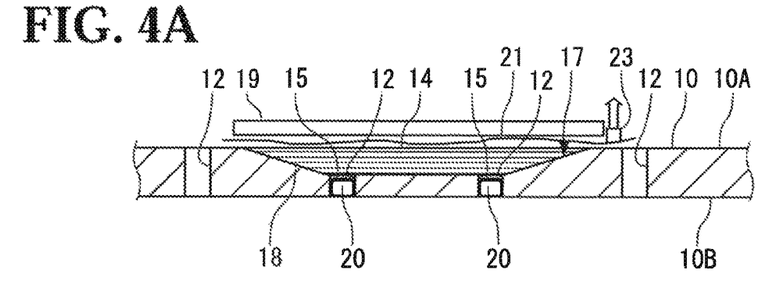
FIG. 4A is a view for explaining a heating step while reducing a pressure.

As shown in FIG. 4A, a film adhesive 18 containing a thermosetting resin is interposed between the repair patch 14 and an inner peripheral surface (the bottom surface 16A and the slanting surface 16B) of the recessed portion 17. The repair patch 14 and the adhesive 18 are heated and cured by using a heater mat 19 or the like.

Here, if a hole is originally formed at a position corresponding to the through-hole 12 in the repair patch 14 formed from the prepreg, and the repair patch 14 is fitted to a shape of the panel 10 by heat-curing, a shape of the hole is changed. Thus, it is difficult to originally form the hole in the repair patch 14.

In the heating, a surface of the repair patch 14 and its peripheral portion are covered with a back film 21, and an internal pressure of the recessed portion 17 is reduced as shown in FIG. 4A. A gap between the back film 21 and a surface of the panel 10 is sealed by a sealant (not shown).

When the internal pressure of the recessed portion 17 is reduced by a vacuum pump (not shown) that is connected to a valve 23 provided at the back film 21, the repair patch 14 is pressed against the panel 10 by a pressure difference with an atmospheric pressure. Thus, the repair patch 14 is shaped such that the surface of the repair patch 14 and the surface of the panel 10 are smoothly continuous without forming a difference in level.

Since an inner portion of the repair patch 14 is densified by the pressure reduction, it is possible to avoid formation of bubbles (voids) on a bonded surface and within the repair patch 14. Accordingly, the repair patch 14 is surely bonded to the panel 10, and the strength/the stiffness are also secured.

It is necessary to form the through-hole 12 into which the fastener 11 is inserted in the repair patch 14 after shaping the repair patch 14. A hole needs to be machined (formed) in the repair patch 14 at the same position as that of the through-hole 12 originally formed in the panel 10 such that the hole continues to the through-hole 12 left in the panel 10 on a back side of the repair patch 14.

Since the through-hole 12 remaining in the panel 10 is concealed on the back side of the repair patch 14, the through-hole 12 cannot be visually recognized from a front side 10A of the panel 10.

In the repair performed in a state in which airframe parts are assembled together, it is difficult to access a back side 10B of the panel 10. Even if the through-hole 12 can be visually recognized by accessing the back side 10B of the panel 10, it is difficult to ensure a working space necessary for machining the hole in the panel 10 and the repair patch 14 through the through-hole 12.

Figure 1E:
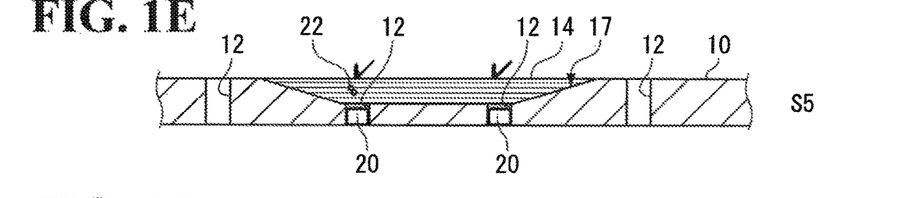

Thus, the position where the hole is machined is located by using the ultrasonic testing that is also used for inspecting a repair quality (FIG. 1E, FIG. 2: step S5). The air AR included in the marker 20 (FIGS. 3A and 3B) previously installed in the through-hole 12 has very different propagation characteristics of ultrasonic waves (referred to as wave propagation characteristics below) from those of the material of the outer shell 20A around the air AR, the fiber reinforced resin used for the repair patch 14 and the panel 10, and the resin of the resin material 15. An ultrasonic testing apparatus makes the marker 20 visible by showing high sensitivity to an interface between the air AR in the marker 20 and its peripheral member where the wave propagation characteristics largely change.

Figure 4B:
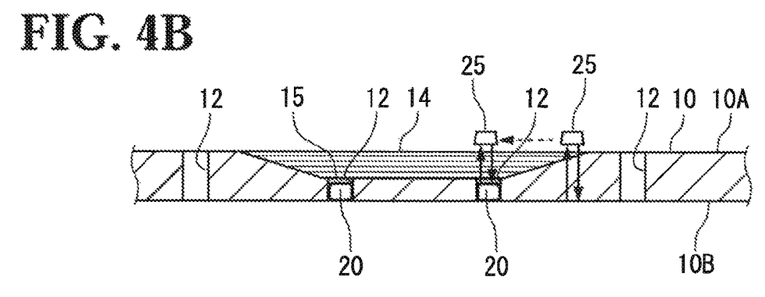
FIG. 4B is a view for explaining a step of locating a hole machining position by ultrasonic testing.

FIG. 4B shows a manner in which the marker 20 is detected by bringing a probe 25 of the ultrasonic testing apparatus into contact with the surface of the repair patch 14, and moving the probe 25 little by little along the surface. The probe 25 oscillates an ultrasonic wave, applies the ultrasonic wave to the repair patch 14 and the panel 10 in the thickness direction, and receives an ultrasonic wave returned from the application target. A signal waveform is displayed on a monitor connected to the probe 25 based on a correlation between the oscillated ultrasonic wave and the received ultrasonic wave. A position of the marker 20 can be easily located based on the signal waveform.

By moving the probe 25, a range in which the air AR exists within the marker 20, that is, a shape and a size of the marker 20 are obtained. Even if a bubble exists within the repair patch 14, the bubble is much smaller than the marker 20. Even when a plurality of bubbles gather, the bubbles are distributed in an irregular shape. It is thus possible to clearly discriminate the bubble from the air AR in the marker 20.

Figure 1F:
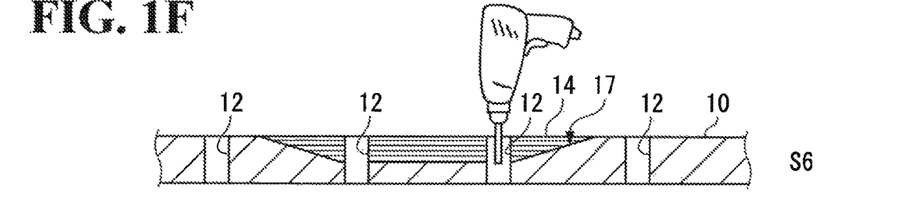

Even when a position where a bubble 22 exists is overlapped with the position of the marker 20 as shown in FIG. 1E, the position where the bubble 22 exists is removed by the hole machining that is subsequently performed as shown in FIG. 1F, and thus, there occurs no problem.

Even when an apparatus that imagines a signal obtained from a range scanned by the probe 25 with the probe 25 self-traveling from an origin position defined on the panel 10 or the repair patch 14 is used, the position of the marker 20 can be easily located based on a difference in shading in a displayed image or the like.

The fibers and the resin in the panel 10/the repair patch 14 have different wave propagation characteristics from those of each other, and the panel 10/the repair patch 14 and the resin material 15 also have different wave propagation characteristics from those of each other. However, the difference in the wave propagation characteristics between the air AR and the panel 10/the repair patch 14/the resin material 15 around the air AR is strikingly larger than the differences. Thus, a position corresponding to the interface between the air AR and its peripheral portion is displayed in a state with a strong contrast without being obscured in the signal waveform or the image. That is, the position of the marker 20 can be located at a position with a strong contrast in the signal waveform or the image.

The located position of the marker 20 corresponds to the position of the through-hole 12. Accordingly, the hole machining position is located. Therefore, the hole is machined throughout the repair patch 14 and the panel 10 at the position of the marker 20 marked on the surface of the repair patch 14, so that the through-hole 12 is formed continuously in the repair patch 14 and the panel 10 (FIG. 1F, FIG. 2: step S6).

At this time, when the hole is machined with a diameter equal to or slightly larger than a diameter of the original through-hole 12, the entire resin material 15 filling the through-hole 12 can be scraped away, and completely removed. At the same time, the marker 20 is also removed.

Through the above steps, the through-hole 12 is formed at the original position. Thus, the fastener 11 (FIG. 1A) is passed through the through-hole 12 to fasten the panel 10 and another member (FIG. 2: step S7), so that the repair is completed.

In accordance with the present embodiment, it is possible to easily locate the accurate hole machining position on the repair patch 14 by the ultrasonic testing by using the marker 20 without preparing an expensive positioning jig or without manually marking a distance from a distinctive portion of the airframe to the fastener 11.

Since the hole machining position can be accurately located, it is possible to avoid a problem in which the hole is formed at a position deviated from the original position due to a measurement error, and the repair needs to be performed again. By machining the hole at the accurate position, it is possible to fully remove the resin material 15 that seals the through-hole 12 without leaving the resin material 15. It is thus possible to avoid a decrease in the stiffness/the strength of the airframe due to the resin material 15 having no strength.

The marker 20 of the present embodiment is not limited to a hollow member including the air AR, and a solid member formed from a metal material may be also employed as the marker.

The wave propagation characteristics of the metal material of the marker and the fiber reinforced resin around the marker 20 differ to an extent that enables the marker 20 to be discriminated from its peripheral portion by the ultrasonic testing. The marker functions similarly to the above marker 20 based on the difference.

It is preferable to prepare a plurality of types of markers having different diameters, as the marker 20, according to the hole diameter of the through-hole 12.

It is also preferable to reduce a thickness of the marker 20 (a dimension along the hole axis of the through-hole 12) in order to respond to a case in which a remaining portion of the panel 10 after the removed region 13 (FIG. 1A) is removed is thin.

Figure 5A:
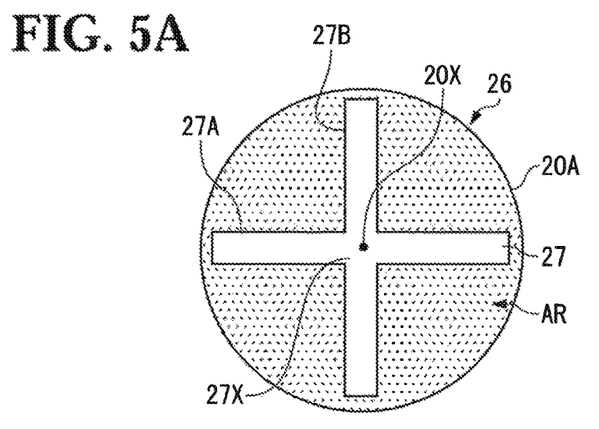
Figure 5B:
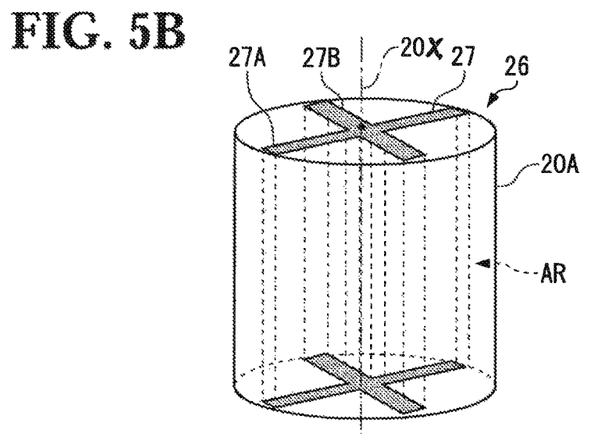

FIGS. 5A and 5B show a marker 26 different from the marker 20 of the above embodiment.

The marker 26 has an indicating member 27 that indicates an axial center 20X of the marker 26 within the outer shell 20A including the air AR. The indicating member 27 can be formed from any material such as resin and metal.

A diameter of the marker 26 may be measured to be larger than an actual diameter depending on measurement accuracy of the ultrasonic testing in some cases. Even in such a case, the axial center of the through-hole 12 is easily located by using the indicating member 27.

The indicating member 27 has a cross shape in which two portions 27A and 27B cross each other at a plane center of the marker 26 through which the axial center 20X of the marker 26 passes. The shape is continuous in a direction of the axial center 20X.

The indicating member 27 may be also formed in a radial shape in which three or more portions cross each other at the plane center of the marker 26.

When the marker 26 is used, the indicating member 27 is made visible from its peripheral portion based on a difference in the wave propagation characteristics between the air AR in the marker 26 and the indicating member 27. Since the marker 26 is arranged within the through-hole 12 such that the axial center 20X substantially corresponds to the axial center of the through-hole 12, an intersection 27X of the indicating member 27 positioned at the axial center 20X of the marker 26 almost exactly indicates the axial center of the through-hole 12.

Therefore, by machining the hole based on a position of the intersection 27X of the indicating member 27 as the center, it is possible to easily form the through-hole 12 at the original position.

Figure 5C:
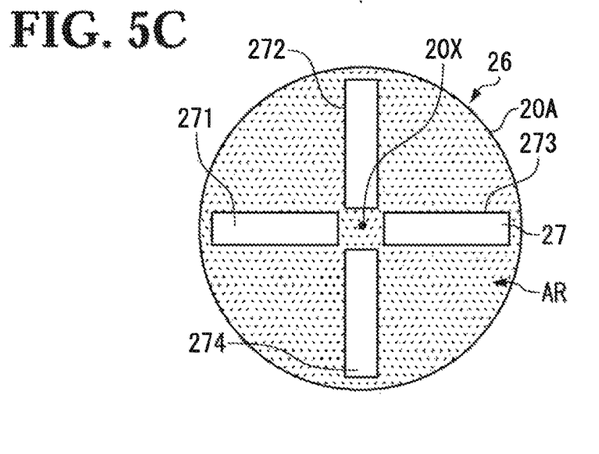

The indicating member 27 of the marker 26 may be missing in the axial center 20X of the marker 26 as shown in FIG. 5C. In this case, four portions 271 to 274 constituting the indicating member 27 also point to the axial center 20X of the marker 26 similarly to FIG. 5A, and indicate the axial center of the through-hole 12 in which the marker 26 is arranged. Thus, the marker 26 functions similarly to the above marker 26.

The marker 26 can be modified into various forms as long as the wave propagation characteristics of the indicating member 27 and the peripheral portion differ to an extent that enables the indicating member 27 to be discriminated from the peripheral portion by the ultrasonic testing.

Figure 6A:
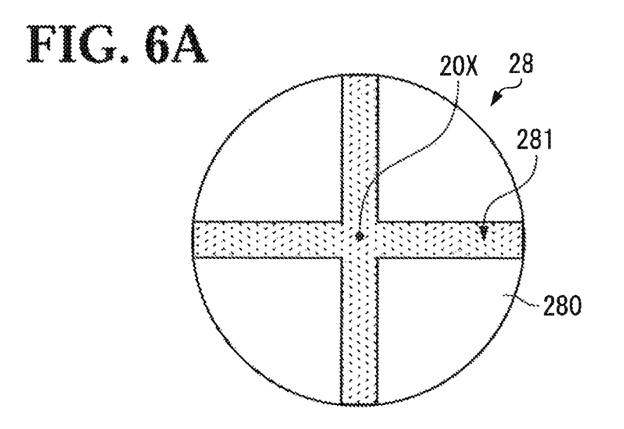
FIGS. 6A to 6C are views illustrating various examples of the marker.

For example, in a marker 28 shown in FIG. 6A, a portion corresponding to the indicating member 27 in FIGS. 5A and 5B is formed as a hollow 281. Since the hollow 281 is formed within a substantially-cylindrical marker body 280 formed from resin or metal, the marker 28 functions similarly to the marker 26 based on a difference in the wave propagation characteristics between the hollow 281 and the marker body 280.

Figure 6B:
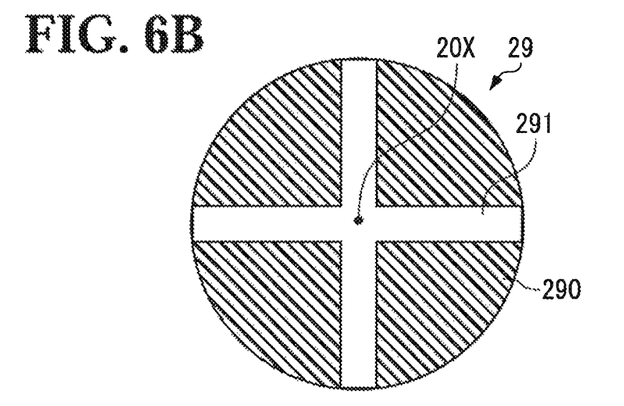

In a marker 29 shown in FIG. 6B, an indicating member 291 formed from a metal material and having a cross shape in section is embedded in a marker body 290 (indicated by diagonal lines) formed from a resin material. The marker 29 also functions similarly to the marker 26 based on a difference in the wave propagation characteristics between the resin material and the metal material.

Figure 6C:
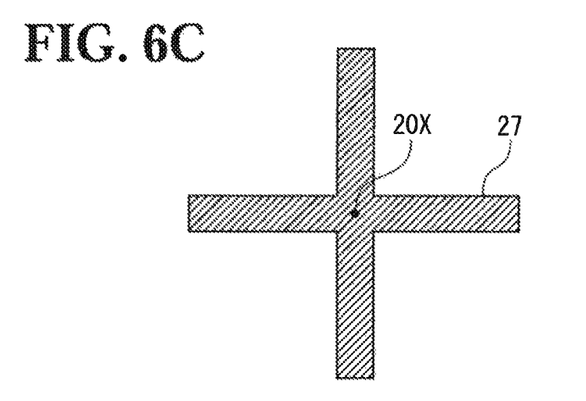

Moreover, even the indicating member 27 alone formed from resin or metal is allowed to function similarly to the marker 26 based on the difference in the wave propagation characteristics between the indicating member 27 and the peripheral portion as shown in FIG. 6C.

A patch obtained by pre-curing a fiber reinforced resin may be used instead of using the repair patch 14 formed from the prepreg, and the patch may be bonded to the panel 10. Moreover, a patch formed from a metal material may be used.

Sheet-shaped fiber substrates may be stacked up in the recessed portion 17 (FIG. 1D), and impregnated with a resin instead of using the repair patch 14.

The present invention is not limited to the embodiment according to the structural member of the aircraft described above, and can be used for repairing general structures formed from a composite material, such as blades of a wind turbine.

There is also a case in which it is not necessary to fill the entire through-hole 12. In this case, for example, a plug 24 having a smaller thickness than a height (a dimension in the thickness direction of the panel 10) of the through-hole 12 can be provided within the through-hole 12 to seal the through-hole 12 as shown in FIG. 3C.

Accordingly, a hollow 120 is ensured in a region other than a portion occupied by the plug 24 in the through-hole 12. Since the position of the through-hole 12 can be located by the ultrasonic testing by using the hollow 120, it is not necessary to arrange the above marker 20 or the like in the through-hole 12.

Figure 3C:
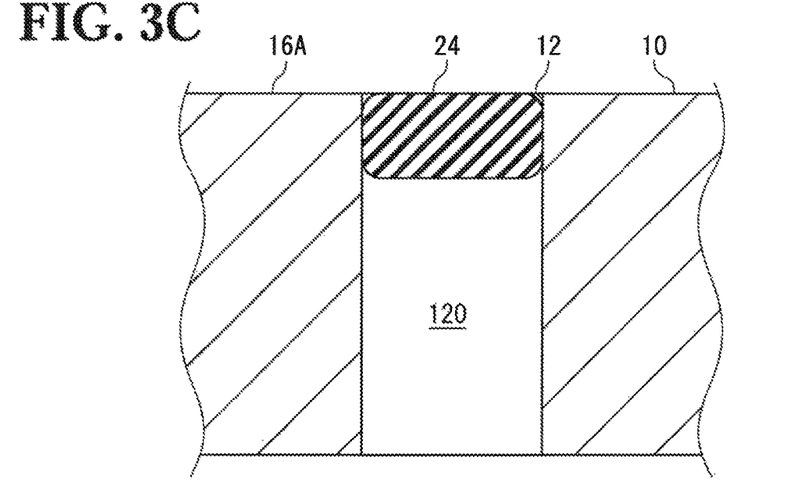
FIG. 3C is a view illustrating another example of a seal material.

In an example shown in FIG. 3C, it is not necessary to remove the resin material 15 (FIG. 3A) filling the through-hole 12 at the time of forming the hole. Thus, the through-hole 12 left in the panel 10 may be directly used without forming a hole again. In this case, a hole continuing to the through-hole 12 may be machined only in the repair patch 14, and the plug 24 may be pushed out by the fastener 11.

Figure 7:
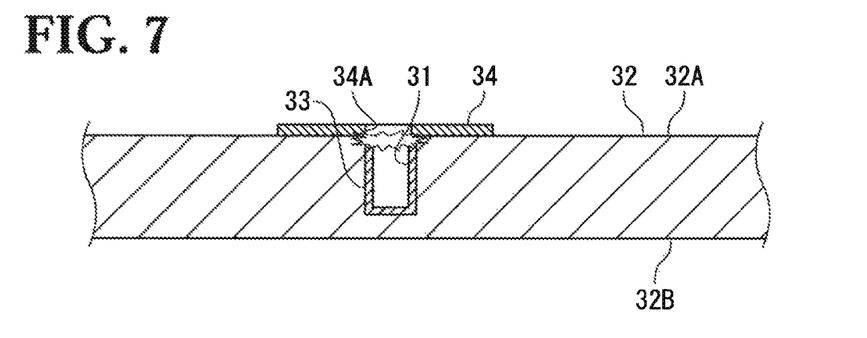
FIG. 7 is a view illustrating a modification of the present invention.

Examples of a machined portion included in a repair region to which the present invention is applied include a non-through hole 31 shown in FIG. 7, a recessed portion, and a depression in addition to the through-hole 12. The hole 31 not reaching a back side 32B of a member 32 needs to be machined from a front side 32A of the member 32. The hole 31 is provided with, for example, a bush 33.

Since an inner portion of the hole 31 existing in the member 32 is hollow, and a position of the hole 31 can be located by performing the ultrasonic testing from a front side of a repair patch 34 that covers the hole 31, a hole may be machined in the repair patch 34 at the position.

In a case of the machined portion, such as the hole 31, that does not pass through the member 32, it is not necessary to seal the hole 31 for vacuum drawing.

A repair material in the present invention is not limited to the one subjected to the pressure reduction in the heat-curing. The repair material is also not limited to the one needed to be cured by heating so as to be joined to a member that is a repair target.

Therefore, even when the machined portion passes through the repair target member, the sealing of the machined portion is appropriately conducted.

The constitutions described in the aforementioned embodiment may be also freely selected or appropriately changed into other constitutions without departing from the gist of the present invention.

What is claimed is:

1. A method for locating a machining position in a repair material that is arranged on a member including a previously machined portion, the method comprising:
    a step of arranging a marker including a portion having a different propagation characteristic of an ultrasonic wave from that of a peripheral portion in the previously machined portion before the repair material is arranged on the member, said marker configured to correspond to the size of the previously machined portion;
    a step of removing a portion of the member after the marker is arranged in the member;
    a step of arranging the repair material on the member; and
    a step of applying the ultrasonic wave to the member covered with the repair material to detect the size of the marker and to locate the machining position at a position of the marker captured by the ultrasonic wave after the repair material is arranged on the member.

2. The method for locating a machining position in a repair material according to claim 1,
    wherein the marker includes air.

3. The method for locating a machining position in a repair material according to claim 2,
    wherein the previously machined portion is a through-hole that passes through the member or a hole that is formed in the member.

4. The method for locating a machining position in a repair material according to claim 1,
    wherein the previously machined portion is a through-hole that passes through the member or a hole that is formed in the member.

5. The method for locating a machining position in a repair material according to claim 4,
    wherein the marker is configured to indicate a machining position of a hole in the repair material which continues to the through-hole that passes through the member or the hole that is formed in the member.

6. The method for locating a machining position in a repair material according to claim 4,
    wherein an inside of the previously machined portion is entirely filled and sealed by the marker and a seal material before the repair material is arranged on the member.

7. The method for locating a machining position in a repair material according to claim 6,
    wherein the seal material is a resin material.

8. The method for locating a machining position in a repair material according to claim 4,
    wherein the marker has an indicating member in a form pointing to an axial center of the marker, or a hollow in a form pointing to the axial center.

9. The method for locating a machining position in a repair material according to claim 1,
    wherein the repair material has a repair patch formed from a fiber reinforced resin before curing.

10. The method for locating a machining position in a repair material according to claim 1,
    wherein the member constitutes an aircraft.

11. A repairing method using a repair material that is arranged on a member including a previously machined portion, the method comprising:
    a first step of arranging a marker including a portion having a different propagation characteristic of an ultrasonic wave from that of a peripheral portion in the previously machined portion before the repair material is arranged on the member, said marker configured to correspond to the size of the previously machined portion;
    a second step of removing a portion of the member;
    a third step of joining the repair material to the member;
    a fourth step of applying the ultrasonic wave to the member covered with the repair material to detect the size of the marker and to locate a machining position at a position of the marker captured by the ultrasonic wave; and
    a fifth step of applying machining to the machining position.

12. The repairing method according to claim 11, wherein the previously machined portion is a through-hole that passes through the member; and the method comprises a sealing step of sealing an inside of the through-hole by a seal material before the repair material is arranged on the member, in the third step, the repair material is cured by heating while a pressure between the repair material and the member is being reduced, and in the fifth step, the marker and the seal material are removed by applying machining to the machining position throughout the repair material and the member.

13. The repairing method according to claim 12, wherein in the sealing step, the inside of the through-hole is entirely filled and sealed by the marker and the seal material.

14. The repairing method according to claim 12, wherein the marker is configured to indicate a position where a hole continuing to the through-hole is machined in the repair material.

15. The repairing method according to claim 12, wherein the marker is configured to retain its shape even when the repair material is heated in the third step, and keep a state in which air is included.

16. The repairing method according to claim 12, wherein after the sealing step and prior to the third step, the member provided with the seal material is mechanically machined.

17. The repairing method according to claim 12, wherein the member with the through-hole being sealed with the seal material is subjected to a mechanical machining for removing a damaged point of the member, after the sealing step and prior to the third step.

* * * * *